US011134911B2

(12) United States Patent
Gündel et al.

(10) Patent No.: US 11,134,911 B2
(45) Date of Patent: Oct. 5, 2021

(54) SUPPORTING AN EVALUATOR IN EVALUATION OF A COMPUTED TOMOGRAPHY DATA SET

(71) Applicant: Siemens Healthcare GmbH, Erlangen (DE)

(72) Inventors: Lutz Gündel, Erlangen (DE); Grzegorz Soza, Heroldsberg (DE)

(73) Assignee: Siemens Healthcare GmbH, Erlangen (DE)

( * ) Notice: Subject to any disclaimer, the term of this patent is extended or adjusted under 35 U.S.C. 154(b) by 0 days.

(21) Appl. No.: 17/023,254

(22) Filed: Sep. 16, 2020

(65) Prior Publication Data

US 2021/0077046 A1 Mar. 18, 2021

(30) Foreign Application Priority Data

Sep. 18, 2019 (DE) ...................... 10 2019 214 212.5

(51) Int. Cl.
*A61B 6/00* (2006.01)
*A61B 6/03* (2006.01)
*G06T 7/11* (2017.01)

(52) U.S. Cl.
CPC .............. *A61B 6/504* (2013.01); *A61B 6/032* (2013.01); *A61B 6/461* (2013.01); *A61B 6/5205* (2013.01);
(Continued)

(58) Field of Classification Search
CPC ......... A61B 6/032; A61B 6/461; A61B 6/504; A61B 6/5205; A61B 2018/00875;
(Continued)

(56) References Cited

U.S. PATENT DOCUMENTS 9,743,835 B2 * 8/2017 Taylor ................ A61B 5/02007
9,788,807 B2 * 10/2017 Schmitt .................. A61B 6/504
(Continued)

OTHER PUBLICATIONS

German Decision to Grant for German Application No. 10 2019 214 212.5 dated Sep. 19, 2019, with English translation.
(Continued)

*Primary Examiner* — Irakli Kiknadze
(74) *Attorney, Agent, or Firm* — Lempia Summerfield Katz LLC (57) ABSTRACT

A method for supporting an evaluator in evaluation of a CT data set of a vascular system is provided. The vascular system is segmented, and an evaluation parameters are determined from the segmentation. An abstracted representation of the vascular system up to the limit generation is displayed, where each vascular segment is allocated at least one display element of a predefined minimum size that is the same for all vascular segments. Display elements of a path from the vascular segment of the zeroth generation to a vascular segment of the limit generation are represented in a first direction of the representation in succession, and display elements of the same generation allocated to different paths follow one another in a second direction transverse thereto. Each display element allocated to a vascular segment is represented in a type of representation corresponding to the value of the evaluation parameter for the vascular segment.

15 Claims, 6 Drawing Sheets

(52) U.S. Cl.
CPC ...... *G06T 7/11* (2017.01); *G06T 2207/10081* (2013.01); *G06T 2207/30101* (2013.01)

(58) Field of Classification Search
CPC ........... A61B 2018/00577; A61B 2018/00791; A61B 17/320068; A61B 2034/2059; A61B 18/1487; A61B 18/1815; A61B 1/0051; A61B 2017/320069; A61B 2017/32007; A61B 6/582; A61B 6/587; A61B 6/12; A61B 6/468; A61B 6/507; A61B 6/5217; A61B 6/5247; A61B 8/0841; A61B 8/461; A61B 8/463; A61B 8/465; A61B 8/468; A61B 8/5238; A61B 6/583; A61B 6/481; A61B 6/00; A61B 6/4035; A61B 6/4042; A61B 6/405; A61B 6/4241; A61B 6/482; A61B 6/548; A61B 5/0044; A61B 5/349; A61B 6/03; A61B 6/4441; A61B 6/463; A61B 6/464; A61B 6/487; A61B 6/027; A61B 6/06; A61B 2090/378; A61B 6/469; A61B 6/488; A61B 6/542; A61B 8/00; A61B 8/08; A61B 8/0816; A61B 8/0891; A61B 8/14; A61B 8/4488; A61B 8/485; A61B 8/5207; A61B 8/4438; A61B 8/5223; A61B 8/54; A61B 2017/00725; A61B 2018/00023; A61B 2034/2063; A61B 2090/3937; A61B 2090/395; G06T 2207/10081; G06T 2207/30101; G06T 7/11; G06T 2200/04; G06T 2207/10088; G06T 2207/30172; G06T 7/68; G06T 2207/10072; G06T 7/0012; G06T 2207/30048; G06T 7/162; G06T 7/12; G06T 7/60; G06T 2207/20104; G06T 2207/20168; G06T 7/62; G06T 11/008; G06T 2211/404; G06T 2207/20081; G06T 2207/20084; G06T 2207/20156; G06T 2207/30032; G01N 33/57492; G01N 33/574; G01N 33/6854; G01N 33/6857; G01N 2223/303; G01N 23/046; G01N 2500/00; A61K 2039/505; A61K 2300/00; A61K 39/39558; A61K 47/6849; A61K 45/06; A61K 47/6803; A61K 51/1027; A61K 31/537; A61K 38/05; A61K 47/6811; A61K 47/6867; A61K 39/3955; A61K 39/395; A61K 31/69; A61K 31/015; A61K 35/28; A61K 35/42; A61K 2039/804; A61K 31/138; A61M 5/007; G06K 2009/4666; G06K 9/00147; G06K 9/46; G06K 9/4604; G06K 9/52; G06K 9/6215; G06K 9/6267; G06K 9/6298; G16H 10/60; G16H 15/00; G16H 30/20; G16H 30/40; G16H 50/50; G16H 40/20; G16H 40/63; G16H 50/20; G16H 50/30; G01R 33/5608; G06F 3/0484; A61N 2007/0095; A61N 7/02; A61N 2007/0052; A61N 2007/027; A61N 2007/0065; A61N 2007/0082; A61N 2007/0091; G21K 1/025; G21K 1/02; G01S 15/8915; G01S 15/892; G01S 15/8927; G01S 15/8952; G01S 15/8959; G01S 15/8997; G01S 7/5202; G01S 7/52046; G01S 7/52085

USPC ........................... 378/1, 4, 8, 19, 57–58, 62
See application file for complete search history.

(56) References Cited

U.S. PATENT DOCUMENTS

| | | | |
|---|---|---|---|
| 2008/0275467 A1* | 11/2008 | Liao ..................... | A61B 6/481 606/130 |
| 2010/0079455 A1* | 4/2010 | Wei ........................ | G06T 19/00 345/424 |
| 2011/0002513 A1* | 1/2011 | Molinari ................ | G16H 30/20 382/128 |
| 2014/0254906 A1* | 9/2014 | Poole ....................... | G06T 7/68 382/131 |
| 2020/0222024 A1* | 7/2020 | Edic ....................... | A61B 6/582 |

OTHER PUBLICATIONS

German Office Action for German Application No. 10 2019 214 212.5 dated Jul. 31, 2020.
Udell, Nicholas. "Algorithms for studying murine airway structure in microfocus computed tomography images." Diss. University of Southampton, 2017. pp. 1-119.

* cited by examiner

SUPPORTING AN EVALUATOR IN EVALUATION OF A COMPUTED TOMOGRAPHY DATA SET

This application claims the benefit of German Patent Application No. DE 10 2019 214 212.5, filed Sep. 18, 2019, which is hereby incorporated by reference in its entirety.

BACKGROUND

The present embodiments relate to supporting an evaluator in the evaluation of a computed tomography data set of a vascular system of a patient.

Vascular systems in patients may yield problems, for example, if inflammatory or other processes restrict the lumen of vessels, or even completely close the lumen. Typical vascular systems in humans include the blood vessel system or corresponding portions, as well as the respiratory tract system (e.g., the bronchi). In terms of the respiratory tract, it has been proposed to use computed tomography (CT) imaging in order to diagnose chronic obstructive lung diseases, to quantify these and, to determine the phenotype. Chronic obstructive lung diseases are often abbreviated to COPD, according to the term "Chronic Obstructive Pulmonary Disease". The recording of computed tomography data sets of the respiratory tract of a patient as a vascular system and the corresponding evaluation allow different quantitative evaluation parameters, which characterize COPD, to be measured. These evaluation parameters include, for example, the wall thickness, the diameter of the lumen, the area of the lumen, the percentage wall area portion of larger airways, and the like. Computed tomography measurements of this kind allow significant regions fluctuations in losses of function of the lungs to be detected, which cannot be detected by other methods (e.g., spirometry). Consequently, a quantitative assessment of this kind may be extremely useful, for example, when selecting candidates for surgical interventions such as lung volume reduction.

The analysis of quantitative evaluation parameters for a highly complex structure such as the tree structure of the respiratory tract is a time-consuming procedure and requires a relatively high mental effort on the part of the evaluator (e.g., a radiologist) in order to consolidate the information into a common mental image of the patient. Consequently, a suitable visualization of the extent and location of the disease is of great interest in order to support radiologists during diagnosis.

According to currently known approaches, the quantitative evaluation parameters are either only recorded in the form of numbers (e.g., concrete values) or are represented in the form of a color-coded visualization of the vascular tree, which may be rendered in three dimensions, for example. In this context, however, there is the problem that, due to the small size of the airways of a higher generation and due to potential masking in the 3D visualization, such an image cannot be interpreted by an evaluator "at a glance". Moreover, the number of branches in the tree structure of the respiratory tract increases with each generation. Since diseases such as COPD mostly may only affect some few vascular segments of the vascular system, this results in an extremely time-consuming diagnosis, as ultimately, every possible path in the tree structure of the vascular system is to be examined individually, even if this only involves the allocation to a pulmonary lobe or sub-lobe, for example. To this end, the color coding usually relates to the generation of the respective vascular segments, which may be selected (e.g., after suitable manual zooming measures) in order to then be examined in more detail for the presences of pathologies in derived representations.

SUMMARY AND DESCRIPTION

The scope of the present invention is defined solely by the appended claims and is not affected to any degree by the statements within this summary.

The present embodiments may obviate one or more of the drawbacks or limitations in the related art. For example, an option for an improved supporting of an evaluator of computed tomography data sets of a vascular system of a patient is provided.

According to the present embodiments, a method includes using a processor to segment the vascular system in the computed tomography data set and, at least for all vascular segments with a generation less than or equal to a limit generation, to determine a quantitative evaluation parameter from the segmentation result. The processor is used to actuate the display means to display a, for example, interactive, abstracted representation of the vascular system up to the limit generation. Each vascular segment is allocated at least one display element of a predefined minimum size that is the same for all vascular segments, and display elements of the vascular segments of a path from the vascular segment of the zeroth generation to a vascular segment of the limit generation are represented in a first direction of the representation in succession. Display elements of the same generation allocated to different paths follow one another in a second direction transverse thereto (e.g., perpendicular thereto). Each display element allocated to a vascular segment is represented in a type of representation corresponding to the value of the evaluation parameter for the vascular segment in accordance with an allocation rule stored in the storage device.

According to the present embodiments, a two-dimensional, intuitive representation that is derived from the computed tomography data set is provided. The computed tomography data set may be intuitively understood by a user (e.g., the evaluator) and represents an excellent basis for further evaluation procedures. The computed tomography data set may also be geared to the objective capabilities of the human eye, as display elements of a sufficient minimum size for perception by the human eye are provided in a targeted manner for all relevant vascular segments, in which, in addition, due to the two-dimensional nature of the representation and the clearly defined arrangement of the display elements, no masking may occur. In this context, the limit generation may lie in the region of five to eight (e.g., at six or seven)). If higher-resolution CT data sets are available, then there is also a desire for taking higher generations into consideration. The resulting abstracted representation of the vascular system, due to the varying type of type of representation of the individual display elements, which is chosen as a function of the value of the quantitative evaluation parameter for the allocated vascular segment, also contains all relevant information such that the abstracted representation may be understood and perceived at a glance. This provides that the evaluator may recognize the presence of any critical values of the evaluation parameter, as appropriate, at a glance, without there being the risk of the evaluator missing vascular segments due to the size being too small, masking, or the like, or of having to awkwardly switch between a wide variety of detailed representations.

The present embodiments therefore provide a novel supporting concept for evaluators, which ascertains quantitative information regarding a vascular system (e.g., the respiratory tract) and visualizes this in a compact and easy-to-interpret manner. The corresponding visualization may serve as the basis for a target-oriented, measurement-based image navigation within the tree structure of the vascular system, which will be discussed in further detail.

Specifically, following the recording of a computed tomography data set, a quantitative evaluation parameter is therefore initially ascertained for each vascular segment of the vascular system. Through the use of an allocation rule, the respective values of the quantitative evaluation parameter may be allocated types of representation, so that in the next act, each of the conceivable paths through the tree structure (e.g., a sequence of vascular segments that may be run through) is projected as a row or column in a representation. For each display element allocated to a vascular segment, which, due to the minimum size, may be clearly recognized regardless of the generation, the corresponding type of representation is chosen. Thus, the extent and the location of a disease may be assessed by the evaluator (e.g., a radiologist) at a glance, so that a diagnostic process that is simpler and less susceptible to errors is produced.

In this context, the technique described here is not restricted to the bronchial system as a vascular system, but rather, may also be applied to other anatomical structures. For example, the technique described may also be applied to portions of the blood vessel system of a patient (e.g., to the coronary tree) in order to ascertain and visualize quantitative information regarding the vascular segments of coronary vessels (e.g., the degree of a stenosis, calcifications, and the like). In all kinds of vascular systems, it is also possible to only take portions into consideration (e.g., particular sub-trees of a vascular system such as the blood system).

In one embodiment, the allocation rule allocates a color to each value of the evaluation parameter as a type of representation. This provides that, in the representation, a color coding may be used as a type of variation of representation that objectively may be well perceived by the human eye and is easy to interpret. In one embodiment, in this context, use is made of a color scale that is oriented toward the criticality of the value of the evaluation parameter (e.g., a color scale that runs from green to red, where the greener colors, which visualize less critical values, transition to yellow and to red hues that visualize highly critical values). Other color scales may also be provided (e.g., the use of blue hues with regard to the bronchial system and the like).

A specific, advantageous development of the present embodiments provides that the evaluation parameter describes a possibly present narrowing of the respective vascular segment (e.g., a diameter of the lumen of the vascular segment divided by an outer diameter of the vascular segment and/or a deviation from a circular shape). The ratio of the overall area of the cross-section of the vascular segment to the area of the lumen thereof would also be conceivable as a specific embodiment of the evaluation parameter. The deviation of the vessel cross-section from a circular shape may indicate a narrowing that may possibly be present, as a structure pressing against the vessel from the outside, for example, may lead to a "denting" and/or changing of the shape to create a somewhat elliptical shape. In this context, the quantitative parameter may be ascertained as an average value across cross-sections along the vascular segment, but may also relate to extreme values (e.g., at the point of the lowest established lumen diameter and/or overall vascular segment diameter). In the case of examination with regard to COPD, the ratio of the diameter of the lumen to the outer diameter may be an evaluation parameter, as the inflammatory processes of COPD usually lead to a thickening of the vascular wall and, as a result, to a reduction in the size of the lumen and/or an enlargement of the outer diameter.

With regard to the displaying of such narrowings (e.g., when examining for possible COPD), for example, a use of a color scale from green to red may be used, where green may describe a large lumen compared to the overall vessel and red may describe a small or no lumen compared to the overall vessel. Ratios may be considered here, as it is then, for example, possible to work with clearly defined values (e.g., between zero and one).

For ascertaining the representation or actuation of the display in concrete terms, in the context of the present embodiments, there exist different variants that may be provided. In this context, the representation may include a matrix-like arrangement of the display elements in the first direction and the second direction, where the generation increases monotonically in the first direction. This provides that the abstracted reproduction of the vascular system is given by a chessboard-like arrangement of display elements that, for example, directly link to one another and, in the first direction (e.g., as columns) indicate possible paths through the vascular system from the zeroth generation up to the limit generation. This provides that the number of columns or rows in the first direction corresponds to the number of possible paths through the vascular system up to the limit generation. The number of rows or columns in the second direction corresponds to the number of generations, accordingly. In this context, the rectangular display element may have a larger extension in the first direction than in the second direction, as in this manner, an association with particularly those vascular segments that are embodied in an elongated manner is given in an a particularly advantageous and intuitive manner. If, for example, the first direction corresponds to the column direction, then it may give the idea that liquid or air would flow through from the top (e.g., zeroth generation) down through the display elements (e.g., along a path).

If it is assumed that, on each division, two new child vascular segments of the next-highest generation are produced, then with a limit generation of six, this provides that there are 128 (e.g., two to the power of six) different paths through the corresponding tree structure. Should there be trifurcations, then there may be provision to map these as two bifurcations. As displays (e.g., screens) may also use a display area that is wider than it is high, it is helpful, even in the general case, to select the first direction as the column direction (e.g., height direction); in this direction, elongated display elements are used, which may then follow one another in rows according to the number of paths without difficulty with sufficient visibility.

In the context of the present embodiments, the paths may be arranged adjacently to one another in the second direction according to any given criteria. Such criteria may include, for example, paths with particular values of the evaluation parameter in a particular generation being arranged adjacently and the like, or even being chosen in a fully randomized manner.

In the context of the present embodiments, however, display elements of child vascular segments originating from the same parent vascular segment may be represented adjacently in the second direction. In this manner, the three-dimensional tree structure of the vascular system is ultimately transformed into a two-dimensional, exceptionally readable structure obtaining adjacency relationships along the paths, so that already at this point, an at least rough spatial allocation is given and, for example, pathologies that extend across adjacent paths also already appear contiguous in the representation. In this manner, an order is consequently detected and integrated into the representation, which ultimately makes it possible to also automate a further mental evaluation step of the evaluator. In other words, the structure of the two-dimensional, abstracted representation, which is embodied such that the abstracted representation may be perceived by the eye and is intuitively readable, is oriented toward the physically existing arrangement of the vascular segments measured by the computed tomography data set.

In a development of this embodiment, it may be provided that display elements adjacent in the second direction of the same vascular segment, but different paths, are consolidated to form one overall element with a common frame. Since, for example, the vascular segment of the zeroth generation, therefore, contributes to each path, the vascular segment of the zeroth generation has a display element for each of the paths, while, for example, two vascular segments of the first generation usually each have display elements for half of the paths. In order to particularly clearly emphasize this belonging to the same vascular segment, and thus in order to enable an improved intuitive readability with regard to associated paths in the generations, it may be provided that these individual display elements are combined to form an overall element (e.g., using a common frame enclosing all these display elements). The readability and legibility of the resulting representation in this embodiment is also increased in that the overall elements, which, for example, are wider (e.g., when the second direction is horizontal), give the impression of the larger vascular segments of a lower generation, which are mostly physically present.

In the matrix-like representation described, it is also possible for subregions of the vascular system to be marked (e.g., by forming spatially separate matrices and/or correspondingly marking the display elements; in the bronchial system, the five pulmonary lobes of the first generation, and/or the nineteen lung segments in generation 2).

Another advantageous development of the present embodiments provides that, in one or more of the at least one display element allocated to one of the vascular segments, the numerical value of the evaluation parameter for this vascular segment is represented. In other words, the values of the quantitative evaluation parameter may likewise be recorded in the diagram formed by the display elements, which enables a deeper quantitative interpretation in combination with the visual representation. If overall elements are used, as has been described, then larger reproductions of the values may also take place in the corresponding regions. For example, the corresponding value of the evaluation parameter may be shown with an overlaid color coding or the like.

In this context, reference is made at this point to the fact that, in addition to the value of the evaluation parameter, for corresponding vascular segments, other information may also be inserted in display elements (e.g., in interaction with the corresponding display element). For example, whenever a mouse cursor rests on a display element or also an overall element, an item of information relating to the corresponding vascular segment (e.g., another ascertained evaluation result, a description of the position/length/orientation, and the like) may be displayed. This may also be applied to the previously mentioned embodiment, in which the value of the evaluation parameter is to be represented in display elements. This representation may also be linked to an interaction with the respective display element (e.g., a "mouseover").

In a development of the present embodiments, it may also be provided that the allocation rule is chosen dynamically as a function of a dynamic range of the values of the evaluation parameter. In one embodiment, the allocation rules may be selected as a function of a further selection parameter. In this manner, the types of representation may ultimately be held in a comparable manner, and the complete available dynamic response (e.g., the entire value range present) may be reproduced in a visually understandable manner. With regard to other selection parameters, the respiratory phase may be used, for example, if the respiratory tract system is the vascular system. In one embodiment, it may be taken into consideration that, when breathing in, an enlargement of the vascular segments may take place, at least of the inner diameter, so that differences in interpretation may occur, which may be compensated by a corresponding adjustment of the allocation rule.

In one embodiment, it may be provided that when the evaluator interacts with a display element from the computed tomography data set, a segmented representation of the allocated vascular segment is generated and displayed (e.g., using an item of examination information describing an examination aim and/or as a function of the evaluation parameter). An interaction of this kind may involve a targeted selection of the display element (e.g., based on a mouse click, tapping on a touch screen as display, and the like). In this manner, the representation using the display elements ultimately serves as a navigation basis, in which the evaluator is able to identify vascular segments of interest in a targeted manner and select the vascular segments for further analysis. The evaluator may be further supported by the computing facility by way of a skillful selection of the segmented representation, which is then produced as a function of the examination aim and/or of the evaluation parameter.

In this context, provision is specifically made, as the segmented representation, for at least one sectional image of the computed tomography data set to be selected as the segmented representation, and/or at least one multiplanar reformation image (MPR image) showing the vascular segment (e.g., also the surrounding area thereof) to be ascertained, and/or a fly-through animation through the lumen of the vascular segment to be rendered as the segmented representation. For example, a segmented representation (e.g., an image), in which the vascular segment may be seen centrally, may, therefore, be generated. Depending on the application case, it is both conceivable to only represent the vascular segment or to also reproduce a surrounding area. The reproduction of the surrounding area makes sense, for example, if anomalies in shape that indicate the presence of an anatomical structure pressing against the vascular segment (e.g., a tumor) are to be examined.

Speaking in general terms, a bronchus or a blood vessel will often be present such that the bronchus or the blood vessel is tilted in relation to the sectional images of the sectional image stack that forms the computed tomography data set, so that a multiplanar reformation (MPR) may be provided in order to be able to represent the vascular segment as completely as possible in a single image as a segmented representation. Other kinds of views may also be generated by MPR in order to support the analysis and, therefore, evaluation in an expedient manner. Rendered representations (e.g., of the vascular segment from the outside or as a "fly-through representation") may also be provided.

In this context, as has already been indicated, the type and/or at least one generating parameter of the segmented representation may be chosen as a function of the examination information and/or of the evaluation parameter and/or an item of interaction information describing the type of the interaction with the display element. It may be inferred from the evaluation parameter, for example, which types of pathologies are to be examined. Additionally, ascertained values of the evaluation parameter may already indicate which pathologies may be present. If, for these pathologies, it is now known, for example, in which segmented representations these may be best recognized, then the suitable segmented representation may now be chosen on a fully automatic basis. The same applies in relation to the examination information, which may also already describe the examination aim, and, therefore, also makes it possible to offer the suitable segmented representation automatically. In one embodiment, different types of interaction with the display element may be allowed, so that a different segmented representation is selected when right-clicking with a mouse, for example, than when left-clicking or middle-clicking. A wide variety of options may be provided in order to support the evaluator, following the intuitive representation using the display elements, for example, serving as a navigation basis, in an even further optimal manner while taking into consideration the examination aim and the conditions actually measured.

As has already been stated, the present embodiments may be applied in a particularly advantageous manner if the vascular system is a respiratory tract system (e.g., with regard to examining for COPD). Other application cases may also be provided, however, so that the vascular system may also be a blood vessel system of the patient.

In addition to the method, the present embodiments also relates to a computing facility that is embodied to perform the method according to the present embodiments. All the statements relating to the method according to the present embodiments may be transferred analogously to the computing facility according to the present embodiments, with which the above mentioned advantages may therefore also be achieved. Accordingly, the computing facility may specifically include at least one processor, at least one storage device, and at least one display. By way of these, corresponding functional units of the computing facility may be implemented (e.g., together with software components). Such functional units may include an evaluation unit, a display unit, and an interaction unit, for example. Specifically, the computing facility may, for example, involve a viewing station for computed tomography data sets and/or a computing facility of an evaluation workstation (e.g., for a radiologist as evaluator).

A computer program according to the present embodiments may be loaded into a storage device of a computing facility, and has program means for carrying out the acts of a method according to the present embodiments when the computer program is executed on the computing facility. The computer program may be stored on an electronically readable data carrier, which therefore includes control information stored thereon; the control information includes at least one computer program according to the present embodiments and is configured such that, when the data carrier is used in a computing facility, the control information carries out the acts of the method according to the present embodiments. The data carrier may involve a non-transient data carrier (e.g., a CD-ROM).

DETAILED DESCRIPTION

Figure 1:
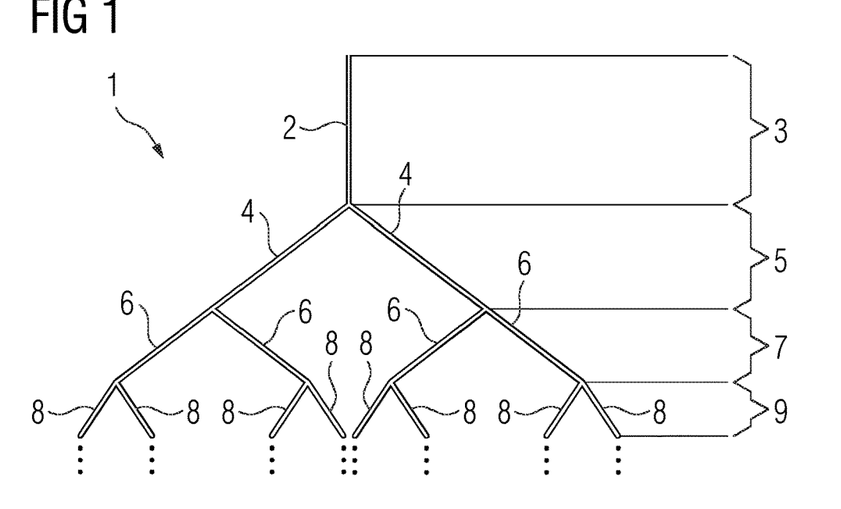
FIG. 1 shows a modeling of a vascular system as a tree structure.

In the following, an exemplary embodiment of the method for an examination of a bronchial system as a vascular system, where the corresponding vessels are then the respiratory tract, is presented. FIG. 1 schematically explains the modeling of the vascular system 1 (e.g., the bronchial system). This is based on the trachea as a first vascular segment 2 of the zeroth generation 3. The trachea serves as a parent vascular segment 2 for the main bronchi as further vascular segments 4 of the first generation 5. The main bronchi may therefore be child vascular segments 4 of the parent vascular segment 2, the trachea. This principle is continued further by the tree structure of the vascular system 1, as shown at the vascular segments 6 of the second generation 7 and the vascular segments 8 of the third generation 9. The continuation dots indicate the further continuation of the division performed in such a way into generations 3, 5, 7, 9 of vascular segments 2, 4, 6, 8.

Figure 2:
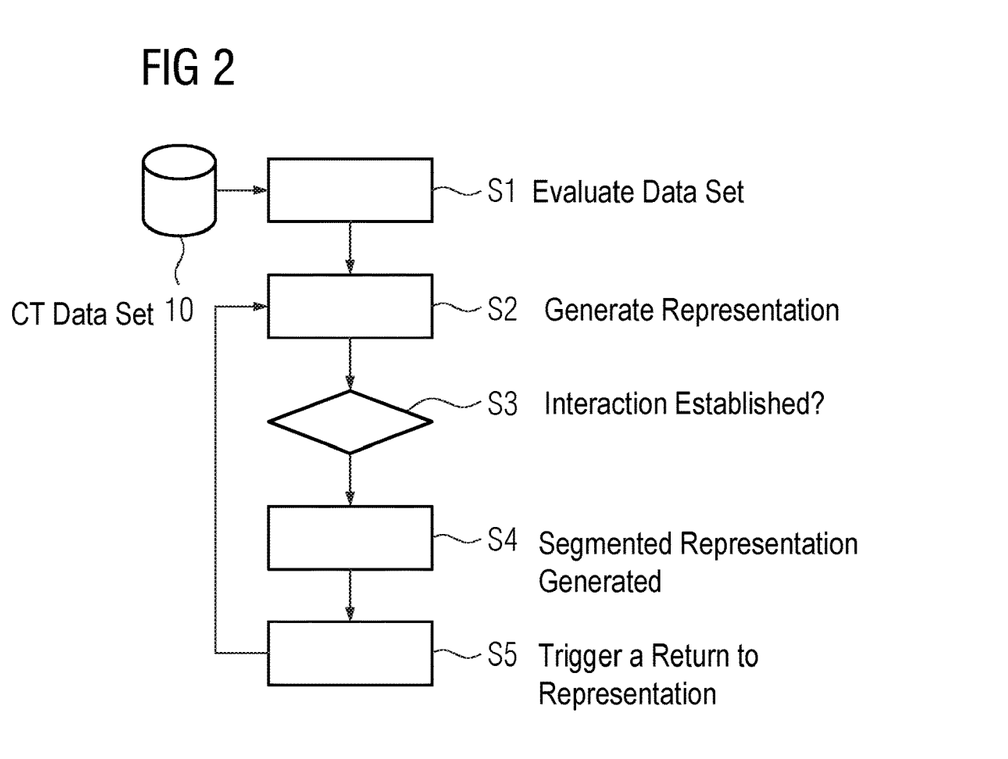
FIG. 2 shows a flow diagram of an exemplary embodiment of a method.

FIG. 2 shows a flow diagram of an exemplary embodiment of the method. This starts from a computed tomography data set 10 of the bronchial system of the patient, which, for example, may exist as a stack of two-dimensional sectional images (e.g., transverse sectional images). In act S1, this computed tomography data set 10 is evaluated by the bronchial system first being segmented through the use of segmentation algorithms that are known in principle, which is easily possible with regard to the lumen, for example, as air has considerably different HU values than the tissue of the bronchial wall (e.g., vascular wall). This excellent segmentability continues in relation to the vascular wall. Next, the modeling described with regard to FIG. 1 is now applied to the segmentation result, which provides that a division of the bronchial system into the various vascular segments 2, 4, 6, 8, . . . of the corresponding generations 3, 5, 7, 9, . . . takes place (e.g., in the present case, up to at least the sixth generation). In the current case, this represents a limit generation. For each of the vascular segments 2, 4, 6, 8 and vascular segments of higher generations, the segmentation result may now be used as a basis for determining quantitative evaluation parameters, which in the present case are to indicate possibly present narrowings in the vascular segment. In this context, in the present exemplary embodiment, the quotient of the inner diameter (e.g., of the diameter of the vascular lumen) and of the outer diameter (e.g., of the overall vascular segment) are taken into consideration.

Alternatively, other parameters (e.g., a deviation from a circular shape) may also be used.

The result of act s1 is, therefore, for each vascular segment 2, 4, 6, 8 and vascular segments of a higher generation, a value of the evaluation parameter, which lies between zero and one in the present case.

In act S2, the evaluation parameter is used to generate an interactive, abstracted representation of the vascular system 1 and to display this on a display (e.g., a screen).

The representation generated in act S2 is two-dimensional and, for each vascular segment 2, 4, 6, 8 and the vascular segments of a higher generation, uses at least one display element of a minimum size; the at least one display element may be easily seen on the screen and offers sufficient space for interaction, as will be explained in further detail below. For each path through the vascular system 1, which is given by successive vascular segments 2, 4, 6, 8 that link to one another and in each case a vascular segment of the generations of a higher generation up to the limit generation, a sequence of display elements running in a first direction is used. This already results in the vascular segment 2 of the zeroth generation 3 being involved in all conceivable paths and, in general, a plurality of display elements being allocated to the vascular segments 2, 4, 6, 8 of a higher generation than the limit generation. The paths themselves, in the representation generated in act S2, are placed next to one another in a second direction perpendicular to the first direction such that display elements allocated to the same generation 3, 5, 7, 9, . . . of vascular segments 2, 4, 6, 8 and to vascular segments of a higher generation follow one another in this second direction. In the representation, the display elements are color-coded according to the values of the evaluation parameters (e.g., on a scale from green to red), where green indicates normal airflow through the airways (e.g., specifically the vascular segments 2, 4, 6, 8 and vascular segments of a higher generation), and transitioning from yellow to red represents an increasing narrowing of the corresponding vascular segments 2, 4, 6, 8 and vascular segments of a higher generation.

Figure 3:
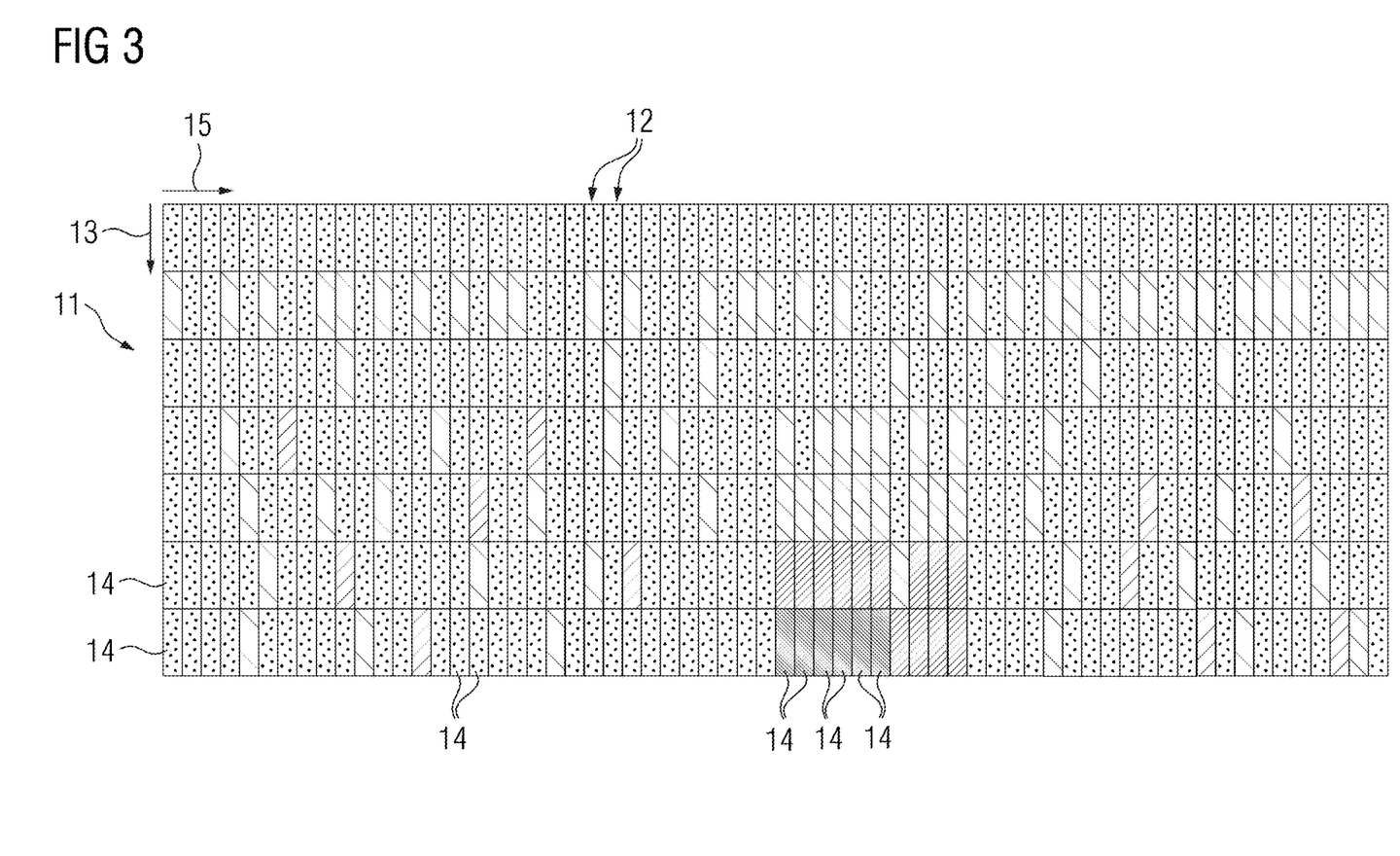
FIG. 3 shows a first visualization option for an evaluation parameter.

FIG. 3 shows a first variant of a representation 11 according to the invention. In this context, the paths 12, represented by the display elements 14 following one another in the first direction 13, are represented such that the paths 12 do not follow one another according to the geometry of the vascular system 1 in the second direction 15. Coloring of the display element 14 is reproduced by various types of crosshatching, where the darkest possible green is represented by dots and the darkest possible green by the closest crosshatching used. The display elements 14', which are allocated to the sixth generation as limit generation, which here serves as limit generation, may be clearly identified, for example.

Figure 4:
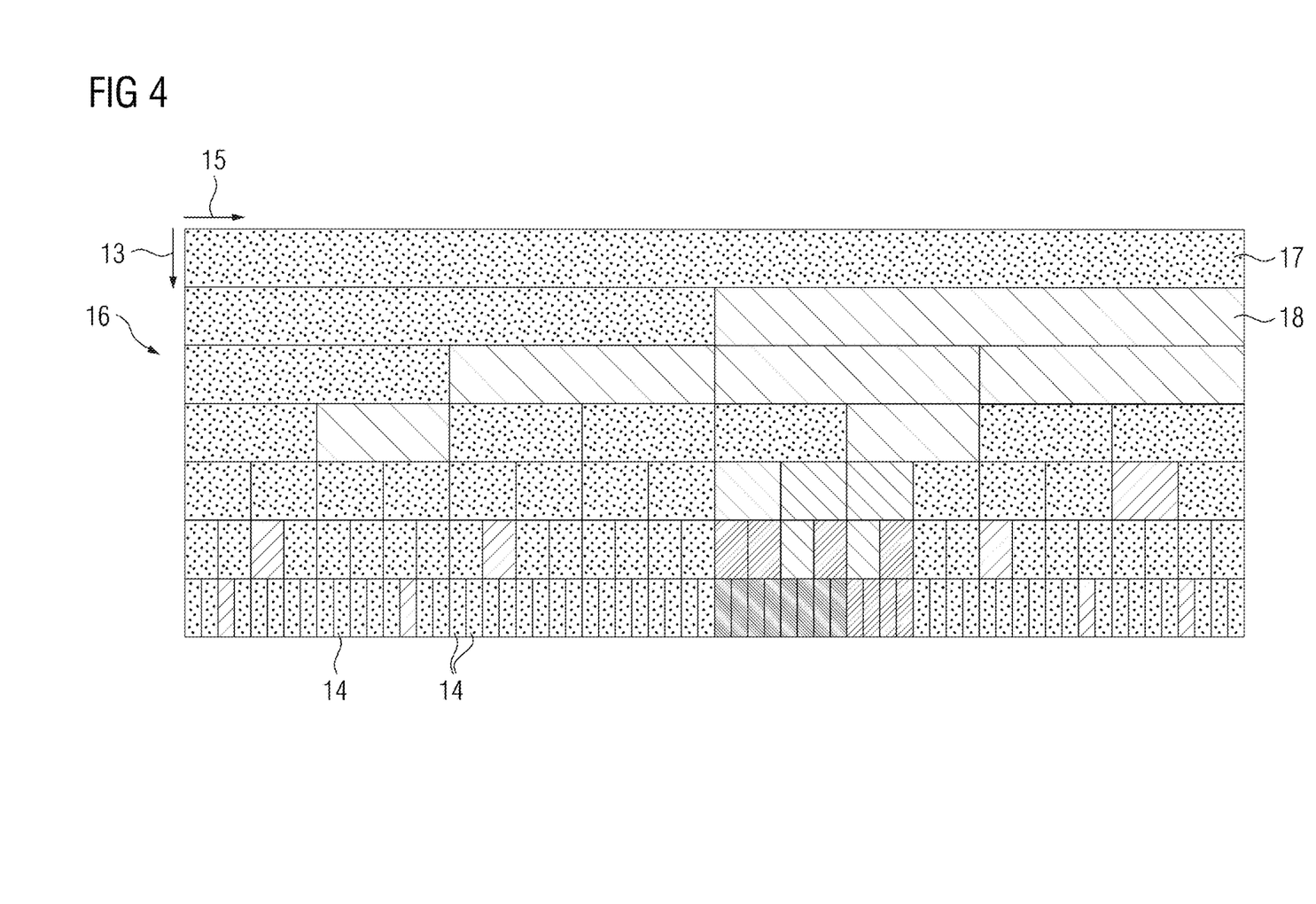
FIG. 4 shows a second visualization option for the evaluation parameter.

FIG. 4 shows a second variant of a representation 16, in which display elements 14 of child vascular segments 2, 4, 6, 8 and vascular segments of a higher generation of the same parent vascular segments 2, 4, 6, 8 and vascular segments of a higher generation are shown next to one another in principle. This makes it possible, as shown in FIG. 4, to consolidate the adjacent display elements, which are allocated to the same vascular segment 2, 4, 6, 8 and vascular segments of a higher generation, to form overall elements with a common frame. This is explicitly emphasized in FIG. 4 for the overall element 17 of the vascular segment 2 of the first generation 3 and the overall elements 18 for the vascular segment 4 of the second generation 5. In this manner, an even more clearly intuitive and readable representation is made possible, which is oriented toward the specific physical conditions ascertained as the segmentation result.

Figures 5, 5A:
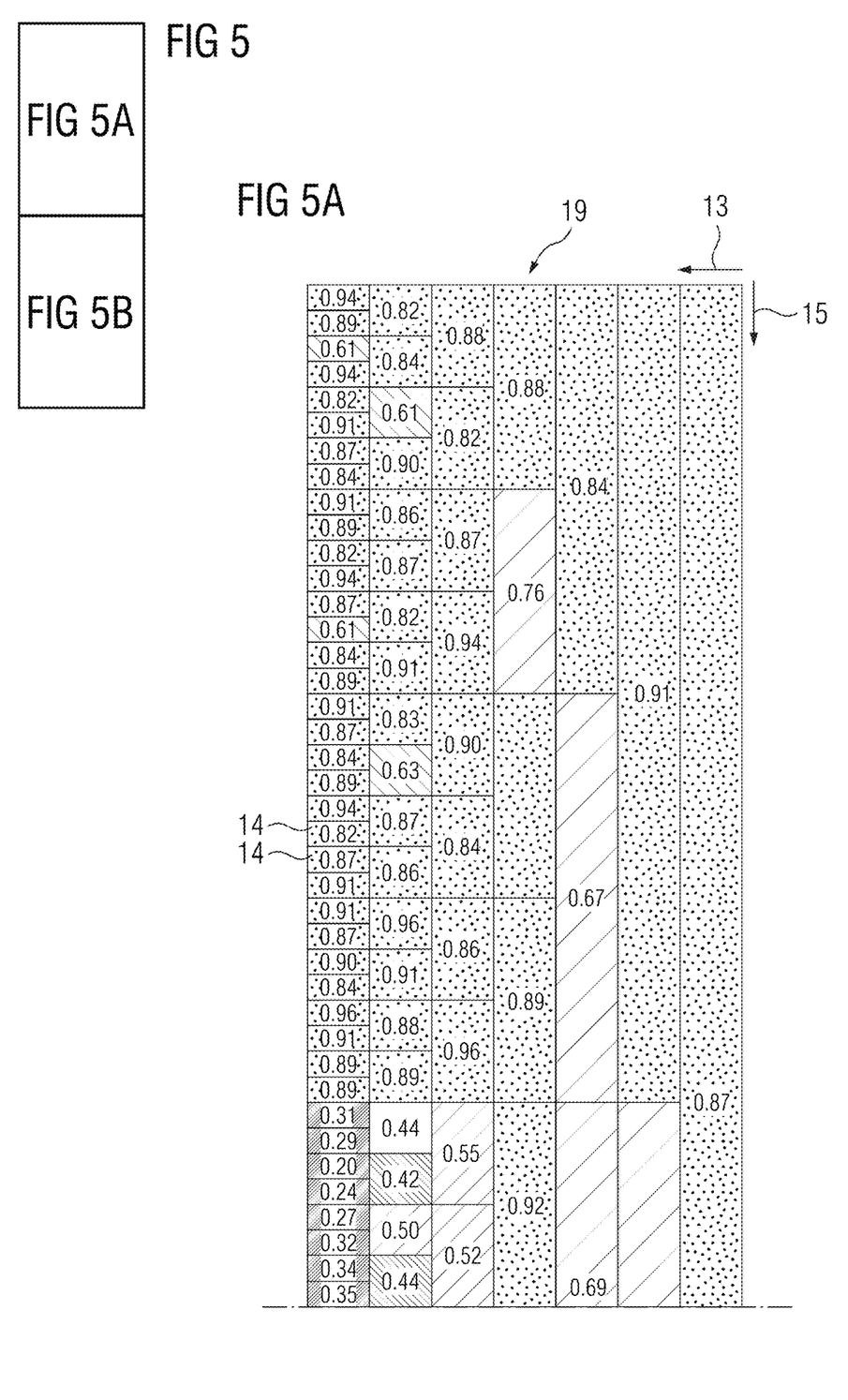
FIGS. 5A and 5B show a third visualization option for the evaluation parameter.
Figure 5B:
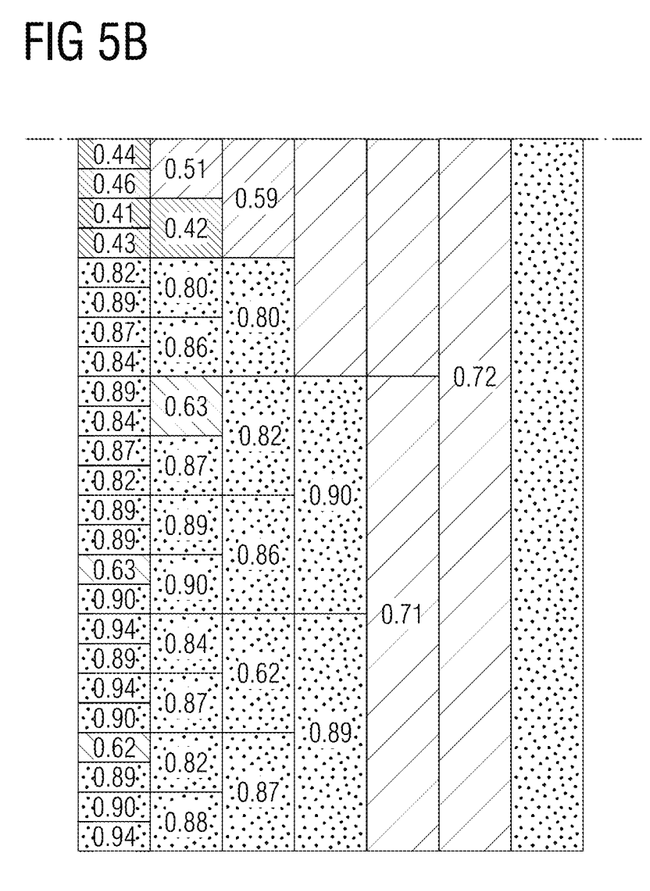

FIG. 5 shows a further variant of a representation 19, which corresponds to the arrangement of the display elements 14 from FIG. 4. Additionally, however, the quantitative values of the evaluation parameter are also entered into the overall elements 17, 18 or display elements 14 accordingly produced in order to provide the evaluator with further information. This display of evaluation information or the value of the evaluation parameter, in other variants, may also be made dependent upon an interaction with the corresponding display element 14 or overall element 17, 18 (e.g., may always be displayed when a mouse cursor is located above the display element 14/overall element 17, 18).

Returning to FIG. 2, in act S3, it is monitored whether an interaction described by an item of interaction information (e.g., a predetermined kind of interaction) of the evaluator with one of the display elements 14 or overall elements 17, 18 is established. If this is the case, then in act S4, a segmented representation relating to the vascular segment 2, 4, 6, 8 selected in such a way and vascular segments of a higher generation is generated (e.g., as a function of an available item of examination information describing the examination aim, which, as appropriate, may also be determined in evaluation act S1, and/or the type of the evaluation parameter or a specific value of the evaluation parameter for the selected vascular segment 2, 4, 6, 8 and vascular segments of a higher generation, and/or the interaction information). For example, different types of interactions of the evaluator with a display element 14/overall element 17, 18 may lead to different types of segmented representations or segmented representations generated with different parameters. In this context, the segmented representation may be an MPR image, for example, in which the selected vascular segment 2, 4, 6, 8 or vascular segments of a higher generation are represented in a centered and complete manner, so that, for example, the plane in which the MPR image is ascertained corresponds to the running plane of the selected vascular segment 2, 5, 6, 8 and vascular segments of a higher generation. Other types of segmented representations include rendered 3D segmented representations, as well as representations in which the surrounding area of the selected vascular segment 2, 4, 6, 8 and vascular segments of a higher generation may also be recognized.

Figure 6:
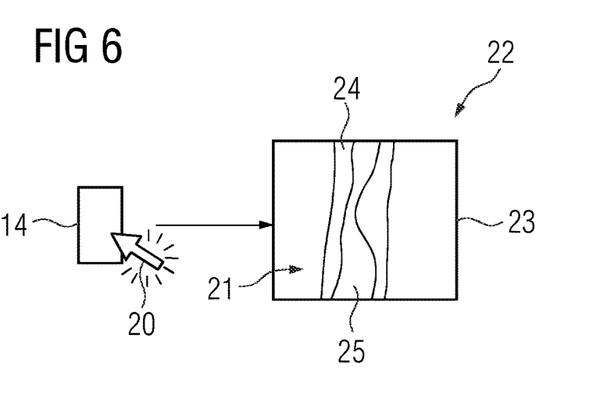
FIG. 6 shows an illustration of the interaction with a representation.

FIG. 6 explains this approach schematically in detail once more. The evaluator uses a mouse cursor 20 to interact (e.g., by clicking) with a display element 14 of a vascular segment 21 of a higher generation (e.g., of the sixth generation), and, by performing acts S3 and S4, due to the fact that the present case involves a COPD examination as the examination aim, the evaluator obtains a segmented representation 22 in the form of an MPR image 23 in the running plane of the vascular segment 21. In this, the evaluator may clearly recognize the course of the vascular wall 24 and of the lumen 25, and may also clearly recognize a narrowing from the thickening of the vascular wall 24.

According to act S5 from FIG. 2, the evaluator is also able to trigger a return to the corresponding representation 11, 16, 19 at any time in order to also be able to analyze other vascular segments 2, 4, 8, 21 in more detail.

Figure 7:
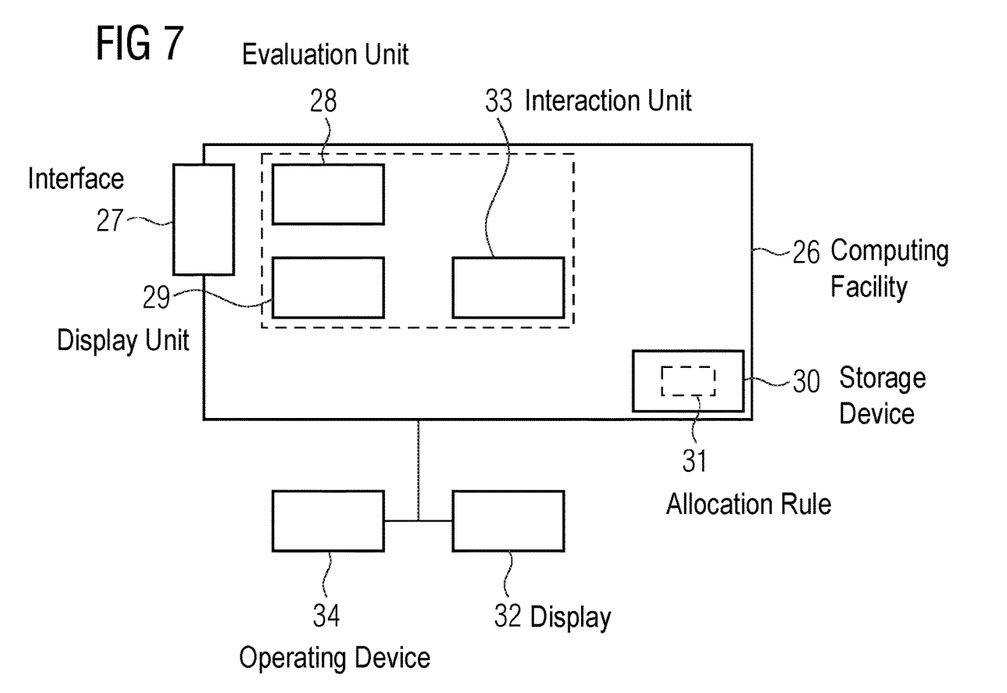
FIG. 7 shows the functional structure of a computing facility according to an embodiment.

FIG. 7 shows the functional structure of a computing facility 26 according to the present embodiments (e.g., a computing facility of an evaluation workstation and/or a viewing station). The computing facility 26 includes an interface 27 for receiving the computed tomography data set 10 (e.g., from a PACS). The evaluations of act S1 may be performed in an evaluation unit 28. A display unit 29 serves to generate one of the representations 11, 16 and 19, as well as a segmented representation, as appropriate, in acts S2, S4. In this context, it is possible to access the allocation rule 31 (e.g., a lookup table) that allocates colors to values of the evaluation parameter (e.g., color table) and is stored in a storage device 30 of the computing facility 26. The display unit 29 may also actuate a display 32 of the computing facility 26 (e.g., a screen). By way of an interaction unit 33, it is possible for interactions of a user (e.g., the evaluator) with the representation 11, 16, 19 to be receive, (see act S3), where the computing facility 26 has a corresponding operating device 34 (e.g., an input device such as a mouse). The display 32 and the operating device 34 may also be provided in an integrated manner as a touch screen, which, for example, enables a direct interaction with display elements 14 using the finger of the evaluator.

Although the invention has been illustrated and described in greater detail with the exemplary embodiments, the invention is not restricted by the examples disclosed, and other variations may be derived therefrom by the person skilled in the art without departing from the protective scope of the invention.

The elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent. Such new combinations are to be understood as forming a part of the present specification.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A method for supporting an evaluator in evaluation of a computed tomography data set of a vascular system of a patient, using a computing facility with a processor, a storage device, and a display, wherein the vascular system has a tree structure starting from a vascular segment of the zeroth generation and, on each splitting of a parent vascular segment of one generation, these link to child vascular segments of a generation one higher, the method comprising:

using the processor to segment the vascular system in the computed tomography data set and, at least for all vascular segments with a generation less than or equal to a limit generation, to determine a quantitative evaluation parameter from a result of the segmentation; and
  using the processor to actuate the display to display an abstracted representation of the vascular system up to the limit generation,
  wherein each vascular segment is allocated at least one display element of a predefined minimum size that is the same for all vascular segments, display elements of the vascular segments of a path from the vascular segment of the zeroth generation to a vascular segment of the limit generation are represented in a first direction of the abstracted representation in succession, and display elements of a same generation allocated to different paths follow one another in a second direction transverse thereto,
  wherein each display element allocated to a vascular segment is represented in a type of representation corresponding to a value of the quantitative evaluation parameter for the vascular segment in accordance with an allocation rule stored in the storage device,
  wherein the abstracted representation comprises a matrix-like arrangement of the display elements in the first direction and the second direction, and
  wherein the generation increases monotonically in the first direction.

2. The method of claim 1, wherein the allocation rule allocates a color to each value of the quantitative evaluation parameter as a type of representation.

3. The method of claim 1, wherein the quantitative evaluation parameter describes a possibly present narrowing of the respective vascular segment.

4. The method of claim 3, wherein the possibly present narrowing of the respective vascular segment includes an outer diameter of the vascular segment divided by a diameter of a lumen of the vascular segment, a deviation from a circular shape, or a combination thereof.

5. The method of claim 1, wherein display elements of child vascular segments originating from the same parent vascular segment are represented adjacently in the second direction.

6. The method of claim 5, wherein display elements adjacent in the second direction of the same vascular segment, but different paths, are consolidated to form one overall element with a common frame.

7. The method of claim 1, wherein, in at least one of the at least one display element allocated to one of the vascular segments, the numerical value of the quantitative evaluation parameter for the one vascular segment is represented.

8. The method of claim 1, wherein the allocation rule is chosen dynamically as a function of a dynamic range of the evaluation parameters.

9. The method of claim 1, wherein, when the evaluator interacts with a display element from the computed tomography data set, a segmented representation of the allocated vascular segment is generated and displayed.

10. The method of claim 9, wherein, when the evaluator interacts with the display element from the computed tomography data set, the segmented representation of the allocated vascular segment is generated and displayed using an item of examination information describing an examination aim, as a function of the evaluation parameter, or a combination thereof.

11. The method as claimed in claim 9, wherein, as the segmented representation, at least one sectional image of the computed tomography data set is selected, at least one multiplanar reformation image showing the vascular segment is ascertained, a fly-through animation through the lumen of the vascular segment is rendered, or any combination thereof.

12. The method of claim 9, wherein the type, at least one generating parameter of the segmented representation, or a combination thereof is chosen as a function of the examination information, the evaluation parameter, an item of interaction information describing the type of the interaction with the display element, or any combination thereof.

13. The method of claim 1, wherein the vascular system is a respiratory tract system or a blood vessel system of the patient.

14. A computing facility configured to support an evaluator in evaluation of a computed tomography data set of a vascular system of a patient, wherein the vascular system has a tree structure starting from a vascular segment of the zeroth generation and, on each splitting of a parent vascular segment of one generation, these link to child vascular segments of a generation one higher, the computing facility comprising:

a processor;
a storage device; and
a display,
wherein the processor is configured to:
  segment the vascular system in the computed tomography data set and, at least for all vascular segments with a generation less than or equal to a limit generation, to determine a quantitative evaluation parameter from a result of the segmentation; and
  actuate the display to display an abstracted representation of the vascular system up to the limit generation,
wherein each vascular segment is allocated at least one display element of a predefined minimum size that is the same for all vascular segments, display elements of the vascular segments of a path from the vascular segment of the zeroth generation to a vascular segment of the limit generation are represented in a first direction of the abstracted representation in succession, and display elements of a same generation allocated to different paths follow one another in a second direction transverse thereto,
wherein each display element allocated to a vascular segment is represented in a type of representation corresponding to a value of the quantitative evaluation parameter for the vascular segment in accordance with an allocation rule stored in the storage device,
wherein the abstracted representation comprises a matrix-like arrangement of the display elements in the first direction and the second direction, and
wherein the generation increases monotonically in the first direction.

15. In a non-transitory computer-readable storage medium that stores instructions executable by one or more processors to support an evaluator in evaluation of a computed tomography data set of a vascular system of a patient, using a computing facility with a processor, a storage device, and a display, wherein the vascular system has a tree structure starting from a vascular segment of the zeroth generation and, on each splitting of a parent vascular segment of one generation, these link to child vascular segments of a generation one higher, the instructions comprising:

using the processor to segment the vascular system in the computed tomography data set and, at least for all vascular segments with a generation less than or equal to a limit generation, to determine a quantitative evaluation parameter from a result of the segmentation; and
using the processor to actuate the display to display an abstracted representation of the vascular system up to the limit generation,
wherein each vascular segment is allocated at least one display element of a predefined minimum size that is the same for all vascular segments, display elements of the vascular segments of a path from the vascular segment of the zeroth generation to a vascular segment of the limit generation are represented in a first direction of the abstracted representation in succession, and display elements of a same generation allocated to different paths follow one another in a second direction transverse thereto,
wherein each display element allocated to a vascular segment is represented in a type of representation corresponding to a value of the quantitative evaluation parameter for the vascular segment in accordance with an allocation rule stored in the storage device,
wherein the abstracted representation comprises a matrix-like arrangement of the display elements in the first direction and the second direction, and
wherein the generation increases monotonically in the first direction.

* * * * *